United States Patent [19]

Ohmori

[11] Patent Number: 4,642,102
[45] Date of Patent: Feb. 10, 1987

[54] INJECTOR

[75] Inventor: Hirofumi Ohmori, Yokohama, Japan

[73] Assignee: Mitsubishi Pencil Co., Ltd., Japan

[21] Appl. No.: 756,852

[22] Filed: Jul. 19, 1985

[30] Foreign Application Priority Data

Jul. 26, 1984 [JP] Japan .................. 59-114118

[51] Int. Cl.⁴ ............................................ A61M 5/00
[52] U.S. Cl. .................................... 604/210; 604/220
[58] Field of Search .............. 604/208, 210, 207, 220; 222/326, 386

[56] References Cited

U.S. PATENT DOCUMENTS

| | | | |
|---|---|---|---|
| 1,569,457 | 1/1926 | Carstens | 604/210 |
| 2,875,761 | 3/1959 | Helmer et al. | 604/210 |
| 4,444,335 | 4/1984 | Wood et al. | 604/208 |
| 4,466,426 | 8/1984 | Blackman | 604/210 |

FOREIGN PATENT DOCUMENTS 711528  6/1965  Canada ................. 604/210

Primary Examiner—John D. Yasko
Attorney, Agent, or Firm—Armstrong, Nikaido, Marmelstein & Kubovcik

[57] ABSTRACT

An injector such as a hypodermic syringe and the like is improved in that an amount of injection each time thereof is mechanically determined by a provision of a stopper means disconnectably attached to a plunger of the injector, which stopper means and the plunger are engaged with each other through a projection-recess engagement thereof, in which engagement the stopper means acts also as a wedge-like means inserted between the plunger and a barrel of the injector to make it possible that the stopper means abutting against a rear end of the barrel at a time when the injection operation is completed prevents the plunger from being advanced beyond it predetermined position, under the effect of its wedge action.

2 Claims, 5 Drawing Figures

INJECTOR

BACKGROUND OF THE INVENTION

1. Field of the Invention

The present invention relates to an injector for injecting a liquid, and more particularly to an improvement of an injector which is employed in any work in which a liquid injecting operation is required, for example such as a hypodermic syringe employed in medical work.

2. Description of the Prior Art

In a conventional injector, a scale is engraved on its barrel or its plunger to make it possible that a user confirms an injection amount of a liquid received in the injector by reading the scale when he advances the plunger to a prescribed position in the injector. Consequently, the conventional injector has a disadvantage in that it is hard to inject an accurate amount of the liquid due to a cumbersomeness in reading the scale and also due to a difficulty in positioning the plunger on a prescribed position accurately in the injector.

In order to resolve the above disadvantage, the applicant of the subject application has previously proposed an injector in his Japanese Utility Model Application No. 27821/1984 as his previous invention, in which injector a stopper means is attached to its plunger in a prescribed position thereof, so that an injection of a precise amount of the liquid received in the injector may be conducted without reading of the scale of the injector by only advancing the plunger in the injector until the stopper means abuts against the barrel of the injector.

However, in such previously proposed injector, it is required to make the stopper means movable in a longitudinal direction of the plunger so as to be adjusted in its position. Consequently, an engagement between the plunger and the stopper means is performed by a provision of a projection-recess engagement and the like engagement so as to make it possible that such engagement is resolved when the stopper means is intentionally and forcibly moved in the longitudinal direction of the plunger, while such engagement produces a click noise when subjected to such resolving action thereof. As a result, in the previously proposed injector, there is a fear that the stopper means is accidentally moved from its engaging position after the stopper means is abutted against the barrel of the injector in the injection operation thereof when a large advancing force is applied to the plunger in its longitudinal direction, so that the injecting amount of the liquid varies from its prescribed value.

SUMMARY OF THE INVENTION

It is an object of the present invention to provide an injector which eliminates the above-mentioned disadvantages and which enables an engagement between a stopper means and its plunger to be made more firm even when an excessively large force is applied to the plunger after the stopper means abuts against the barrel of the injector in its injection operation, so that there is no fear that the stopper means is accidentally moved from its engaging position on the plunger, whereby it is possible to inject the liquid by an accurate amount, which stopper means is attached to the barrel of the injector.

In other words, it is an object of the present invention to provide an injector in which a stopper means is attached to an outer peripheral portion of the plunger of the injector so as to be movable in a longitudinal direction of the plunger, which stopper means abuts against a rear end surface of the barrel of the injector so as to stop an advancing movement of the plunger, wherein the injector is characterized in that: a plurality of recesses which are spaced apart from each other at intervals of a certain distance in the longitudinal direction of the plunger are provided in the outer peripheral portion of the plunger; projections are provided in a front end portion of the stopper means so that the projections are brought into engagement with such recesses; at least one of the barrel of the injector and the stopper means provides an oblique surface in its engaging portion; whereby an attaching force of the stopper means to the plunger in its recesses is increased under the effect of a component force directed in a direction perpendicular to the longitudinal direction of the plunger, which component force is produced in the above oblique surface from an advancing force of the plunger in its longitudinal direction at a time when the injection operation is performed, under a condition in which the stopper means abuts against the barrel of the injector.

BRIEF DESCRIPTION OF THE DRAWINGS

The present invention will now be described by way of example with reference to the accompanying drawings in which.

DESCRIPTION OF THE PREFERRED EMBODIMENTS

Figure 1:
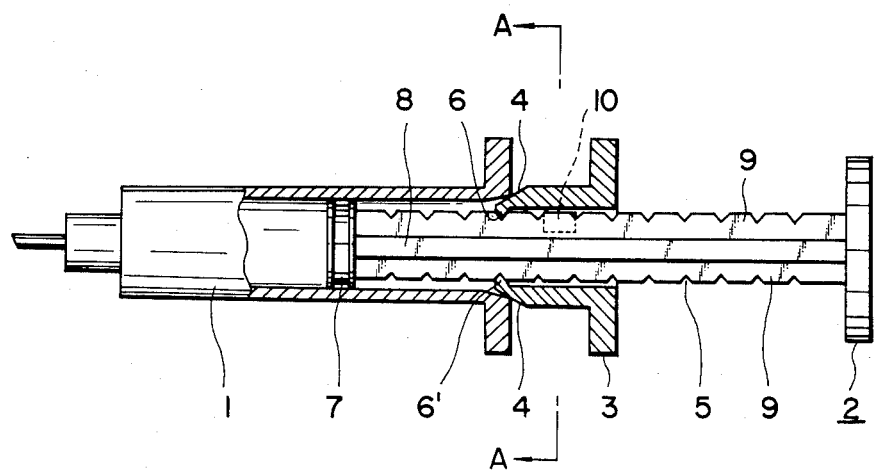
FIG. 1 is a partially longitudinally sectional front view of the injector of the present invention.
Figure 2:
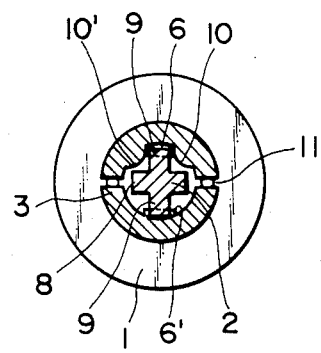
FIG. 2 is a cross sectional view of the injector of the present invention, taken along the line A—A in FIG. 1.
Figure 3:
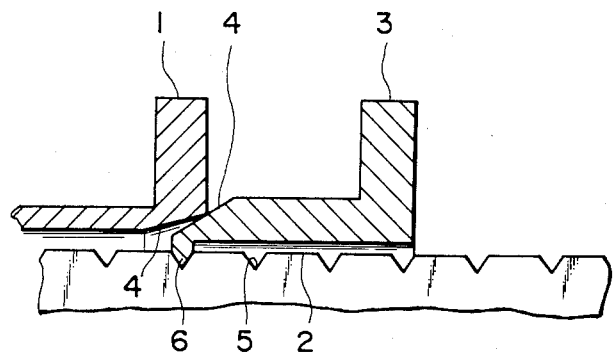
FIG. 3 is a partially enlarged front view of the stopper means and the barrel of the injector of the present invention in their engaging condition.

As shown in FIG. 1, in an injector of the present invention, a stopper means 3 is mounted on an outer peripheral surface of a plunger 2 of the injector so as to be movable in a longitudinal direction of the plunger 2 so that the stopper means is brought into an abutting engagement with a rear end surface of the barrel 1 of the injector in its injection operation so as to prevent the plunger 2 from being advanced beyond its prescribed position, wherein, at least one of the barrel 1 and the stopper means provides an oblique surface 4 in its engaging portion, which oblique surface 4 is so shaped that a thickness of the stopper means 3 decreases in an advancing direction of the plunger 2 so that a front end of the stopper means 3 has a wedge-like shape as shown in FIG. 1. The plunger 2 is provided with a sealing portion 7 in its front end and a shaft portion 8 in its middle portion, which shaft portion 8 is provided behind the sealing portion 7 and has a cross-like shape in its cross section as shown in FIG. 2, while the shaft portion is provided with its rib parts 9. A pair of diametrically opposite rib parts 9 have a plurality of recesses 5 on their outmost surfaces, which recesses 5 are spaced apart from each other at intervals of a certain distance in a longtiudinal direction of the shaft portion 8 of the plunger 2. The stopper means 3 is provided with an inner hole in which a pair of projections 10, 10' are provided so as to be spaced apart from each other at a distance slightly larger than a width of the rib part 9 of the plunger 2 in an upper portion of such inner hole of the stopper means 3, which projections 10, 10' are laterally opposite to each other and have curved convex shapes. A pair of another projections 6, 6' are provided in the inner hole of the stopper means 3 in its front edge portion so as to be diametrically opposite to each other. The above-mentioned oblique surface 4 is provided so as to be placed in a reverse side of a portion of the stopper means 3, in which portion is provided each of the projections 6, 6' as clearly shown in FIG. 3.

It is possible to provide another oblique surface in a rear end portion of the barrel 1 in its inner peripheral surface, and also possible to eliminate one of these oblique surfaces from the stopper means 3 or the barrel 1 of the injector.

The stopper means 3 is mounted on the outer peripheral surface of the plunger 2. Under a condition in which the plunger 2 is inserted into the inner hole of the stopper means 3 so that one of the rib parts 9 of the shaft portion 8 of the plunger 2 is placed between the projections 10, 10' of the stopper means 3, the projections 6, 6' of the stopper means 3 are ready for engagement with the recesses 5 of the rib parts 9 of the plunger 2. Under such condition, when the stopper means 3 is moved in a longitudinal direction of the plunger 2, the projections 6, 6' of the stopper means 3 are brought into engagement with the recesses 5 of the rib parts 9 of the plunger 2 to produce a click noise.

The above embodiment of the present invention may be modified as follows: namely, in contrast with the above embodiment of the present invention, the recesses are provided in a front end portion of the stopper means 3, while a plurality of projections, which are inserted into the above recesses of the stopper means 3, are provided in the outer peripheral surface of the plunger 2 so as to be spaced apart from each other at intervals of a certain distance in a longitudinal direction of the plunger 2, whereby the same engaging effect as that obtained in the above embodiment of the present invention may be obtained.

Figure 4:
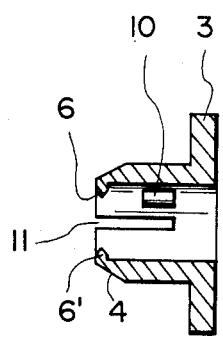
FIG. 4 is a longitudinal sectional view of the stopper means.
Figure 5:
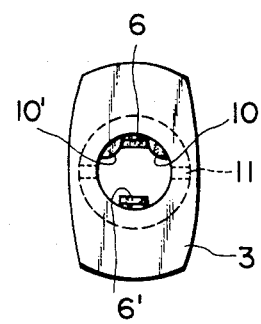
FIG. 5 is a right side view of the stopper means.

As shown in FIG. 4, the stopper means 3 is provided with at least one slit 11 in its front end portion in which is provided the projections 6, 6', which slit 11 extends toward a rear flange portion of the stopper means 3, so that the slit 11 facilitates the engagement between the projections 6, 6' and the recesses 5 of the rib parts 9 of the plunger 2.

When the projections 6, 6' of the stopper means 3 engage with the recesses 5 of the rib parts 9 of the plunger 2, a click noise is produced by such engagement, which click noise enables the user to confirm a completion of an injection operation of a prescribed amount of the liquid received in the injector, without his reading the scale of the injector.

If necessary, it is possible to freely move the stopper means 3 relative to the plunger 2 in its longitudinal direction by rotating the plunger 2 relative to the stopper means 3 by applying a relatively large force to the plunger 2 so as to make it possible that the rib parts 9 of the plunger 2 get over the projections 10, 10' of the stopper means 3 so that the engagement between the projections 6, 6' and the recesses 5 of the rib parts 9 of the plunger 2 is resolved. The projections 10, 10' of the stopper means 3 act as means for surely keeping a condition of engagement/disengagement between the projections 6, 6' of the stopper means 3 and the recesses 5 of the plunger 2.

The shape of the shaft portion 8 of the plunger 2 may be modified so that the shaft portion 8 of the plunger 2 has, in its cross section, a circular shape, a three-pronged shape, or a five or more-pronged shape. In case that the shaft portion 8 of the plunger 2 has a circular shape in its cross section, the recesses 5 are provided in the outer peripheral surface of the shaft portion 8 of the plunger 2 so as to form a rack-like shape thereon, while in order to receive the projections 10, 10' of the stopper means 3 there are provided concave portions in suitable positions of the shaft portion 8 of the plunger 2.

Further, in case that the shaft portion 8 of the plunger 2 has a three-pronged shape in its cross section, the recesses 5 are provided in any two of three prongs of the shaft portion 8 of the plunger 2 in its cross section, while the projections 6, 6' of the stopper means 3 are provided in positions corresponding to those of the recesses 5 of the shaft portion 8 of the plunger 2. In this case, one or two of the projections 10, 10' of the stopper means 3 may be provided so as to be inserted between such prongs or the rib parts 9 of the shaft portion 8 of the plunger 2.

In case that five prongs or five rib parts 9 are employed in the shaft portion 8 of the plunger 2, the recesses 5 of such prongs of the plunger 2 and the projections 10, 10' of the stopper means 3 may be provided in the same manner as that in the case of the three-pronged shape of the shaft portion 8 of the plunger 2 in its cross section mentioned above.

In use, the injector of the present invention acts as follows:

At first, the rib part 9 of the plunger 2, which is provided with the recesses 5, is inserted between the projections 10, 10' of the stopper means 3 so that the engagement between the projections 6, 6' of the stopper means 3 and the recesses 5 of the rib part 9 of the plunger 2 is surely established. Then, the plunger 2 is fully advanced to the front end of the barrel 1 of the injector while the stopper means 3 is attached to a rear end portion of the plunger 2, and thereafter the plunger 2 is moved rearward relative to the barrel 1 of the injector so that the liquid for injection use is introduced into the barrel 1 of the injector.

The plunger 2 is then slightly advanced again relative to the barrel 1 of the injector for expelling the air from the barrel 1 of the injector as required. Thereafter, the stopper means 3 is adjusted in its longitudinal position in the plunger 2 according to an injecting amount of the liquid by moving the stopper means 3 relative to the plunger 2 in its longitudinal direction so that the thus positioned stopper means 3 gives the plunger 2 a predetermined stroke corresponding to a prescribed amount of the liquid for injection use by abutting in its front end against a rear end surface of the barrel 1 of the injector, wherein the position of the stopper means 3 on the plunger 2 is fixed through the engagement between the projections 6, 6' of the stopper means 3 and the recesses 5 of the plunger 2. Then, the plunger 2 is advanced in the barrel 1 of the injector until the stopper means 3 abuts against the rear end surface of the barrel 1 of the injector so that a prescribed amount of the liquid received in the barrel 1 of the injector is accurately injected into an object of injection.

At this time, there is no fear that the stopper means 3 is accidentally moved relative to the plunger 2 in a condition in which the stopper means 3 abuts against the rear end surface of the barrel 1 of the injector even when the plunger 2 is subjected to a further advancing force by mistake, because such further advancing force applied to the plunger 2 is received by the oblique surface 4 which transforms such further advancing force into an engaging force directed in a direction perpendicular to the longitudinal direction of the plunger 2, through which engaging force the projections 6, 6' of the stopper means 3 are brought into a more firm engagement with the recesses 5 of the plunger 2, so that there is no fear that the liquid is excessively injected into the object of injection.

Incidentally, as described above, it is possible to provide such oblique surface 4, which is provided in the stopper means 3, in the barrel 1 of the injector in place of the stopper means 3 so that the same effect as that obtained in the case where the oblique surface 4 is provided in the stopper means 3 is obtained.

In case that such oblique surface 4 is provided in each of the stopper means 3 and the barrel 1 of the injector, the stopper means 3 may abut against the barrel 1 of the injector in a more smooth manner.

Since the injector of the present invention has the above-mentioned construction, it is possible to precisely inject a prescribed amount of the liquid received in the barrel 1 of the injector in an easy manner without requiring the reading of the scale of the injector by advancing the plunger 2 of the injector relative to the barrel 1 of the same until the stopper means 3, which is fixed to a predetermined position of the plunger 2 of the injector, abuts against the barrel 1 of the injector.

In a condition in which the stopper means 3 abuts against the the barrel 1 of the injector, when the plunger 2 of the injector is subjected to a further advancing force thereof, such further advancing force of the plunger 2 is divided into its component forces through the oblique surface 4 provided in the engaging portions of the stopper means 3 and the barrel 1 of the injector, one of which component forces is directed in a direction perpendicular to the longitudinal direction of the plunger 2 of the injector and acts on the projections 6, 6' of the stopper means 3 so as to increase an urging force or engaging force of such projections 6, 6' to the recesses 5 of the plunger 2 of the injector, wherein the more such further advancing force of the plunger 2 of the injector increases, the more the engaging force between the stopper means 3 and the plunger 2 becomes firm, so that there is no fear that a mistake is happened in the injection operation of the injector as to the injecting amount of the liquid, whereby it is ensured that a prescribed amount of the liquid is precisely injected into the object of injection at any time it is required. This is a remarkable effect of the injector of the present invention.

What is claimed is:

1. An injector comprising:

a barrel;

a plunger advanceable in said barrel and having a shaft portion and a sealing portion; and stopper means mounted on an outer peripheral portion of said shaft portion of said plunger so as to be movable in a longitudinal direction of said plunger, for abutting against a rear end surface of said barrel upon said plunger being advanced a predetermined distance in said barrel;

a front end portion of said stopper means being provided with inwardly extending projections formed thereon, and an outer peripheral surface of said plunger shaft portion being provided with recesses formed therein at intervals of a certain distance therealong in the longitudinal direction thereof, said projections and recesses being engageable with each other;

respective engaging portions being formed in said rear end surface of said barrel and on said front end of said stopper means for abutting engagement therebetween, at least one of said respective engaging portions of said barrel and stopper means being shaped into an oblique surface with respect to the longitudinal direction of said plunger; and at least one slit being provided in said front end portion of said stopper means, said at least one slit extending longitudinally towards a flange of said stopper means;

whereby, in a condition of abutting engagement between said respective engaging portions of said barrel and said stopper means under application of an advancing force upon said plunger acting in the advancing longitudinal direction thereof relative said barrel, said advancing force is received by said at least one oblique surface and translated thereby into an engaging force directed perpendicularly to said longitudinal direction of said plunger by which engaging force said projections on the stopper means are brought into a more firm engagement with said recesses in said plunger shaft portion such that said engaging force therebetween increases as said advancing force upon said plunger increases.

2. An injector comprising:

a barrel;

a plunger advanceable in said barrel and having a shaft portion and a sealing portion; and stopper means mounted on an outer peripheral portion of said shaft portion of said plunger so as to be movable in a longitudinal direction of said plunger, for abutting against a rear end surface of said barrel upon said plunger being advanced a predetermined distance in said barrel;

a front end portion of said stopper means being provided with recesses formed therewithin, and an outer peripheral surface of said plunger shaft portion being provided with outwardly extending projection formed thereon at intervals of a certain distance therealong in the longitudinal direction thereof, said recesses and projections being engageable with each other;

respective engaging portions being formed in said rear end surface of said barrel and on said front end of said stopper means for abutting engagement therebetween, at least one of said respective engaging portions of said barrel and stopper means being shaped into an oblique surface with respect to the longitudinal direction of said plunger; and at least one slit being provided in said front end portion of said stopper means, said at least one slit extending longitudinally towards a flange of said stopper means;

whereby, in a condition of abutting engagement between said respective engaging portions of said barrel and said stopper means under application of an advancing force upon said plunger acting in the advancing longitudinal direction thereof relative said barrel, said advancing force is received by said at least one oblique surface and translated thereby into an engaging force directed perpendicularly to said longitudinal direction of said plunger by which engaging force said recesses in said stopper means are brought into a more firm engagement with said projections on said plunger shaft portion such that the engaging force therebetween increases as said advancing force upon said plunger increases.

* * * * *